US005502074A

United States Patent [19]

Cullinan et al.

[11] Patent Number: 5,502,074
[45] Date of Patent: Mar. 26, 1996

[54] BENZOTHIOPHENES FOR BONE HEALING AND FRACTURE REPAIR

[75] Inventors: George J. Cullinan, Trafalgar; Masahiko Sato, Carmel, both of Ind.

[73] Assignee: Eli Lilly and Company, Indianapolis, Ind.

[21] Appl. No.: 294,130

[22] Filed: Aug. 22, 1994

[51] Int. Cl.[6] .................................................. A61K 31/38
[52] U.S. Cl. .................................................. 514/443
[58] Field of Search ................................. 514/333, 443

[56] References Cited

U.S. PATENT DOCUMENTS

| 4,133,814 | 1/1979 | Jones et al. | 260/326.55 |
|---|---|---|---|
| 4,380,635 | 4/1983 | Peters | 546/202 |
| 4,418,068 | 11/1983 | Jones | 424/267 |
| 5,075,321 | 12/1991 | Schreiber | 514/337 |
| 5,393,763 | 2/1995 | Black et al. | 514/333 |

FOREIGN PATENT DOCUMENTS

| 93/584952 | 3/1994 | European Pat. Off. . |
| WO93/10113 | 5/1993 | WIPO . |
| WO93/1074 | 6/1993 | WIPO . |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomzed Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti–estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB–3 Expression in Bone;" Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al, "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L. J. "Biological Actions and Binding Properties of a New Estrogen Antagonist LY117018," In: Homone Antagonists, 129–82, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Admininstration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–naphthalenyl] [4–[2–pyrrolidinyl) ethoxyl]–phenyl] methanone, methanesulfonic acid salt, Journal of Medicinal Chemistry 22;1979, 962–966.

(List continued on next page.)

Primary Examiner—Theodore J. Criares
Attorney, Agent, or Firm—James J. Sales; David E. Boone

[57] ABSTRACT

A method of facilitating bone healing and fracture repair comprising administering to a human in need thereof an effective amount of a compound having the formula

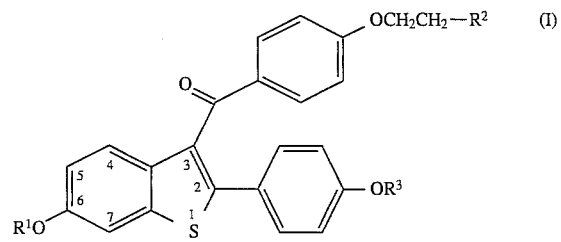

wherein $R^1$ and $R^3$ are independently hydrogen,

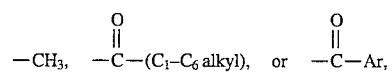

wherein Ar is optionally substituted phenyl;

$R^2$ is selected from the group consisting of pyrrolidine, hexamethyleneamino, and piperidino; or a pharmaceutically acceptable salt of solvate thereof.

3 Claims, No Drawings

OTHER PUBLICATIONS

Black et al., Antiestrogens 2. Structure Activity Studies in a Series of 3-Aroyl-2-arylbenzo[b]thiophene Derivatives Leading to [6-Hydroxy-2-(4-hydroxyphenyl)benzo[b]thien-3-yl][4-2-(1-piperidinyl)ethoxy]-phenyl]methanone Hydrochloride (LY156758), a Remarkably Effective Estrogen Antagonist with Only Minimal Intrinsic Estrogenicity, J. Med. Chem. 27(8), 1984, 1057–1066.

Bolander et al., "Estrogen Treatment During Fracture Repair Strengthens Healing Cellous In an Osteoporotic Model," 38th Annual Meeting, Orthopredic Research Society, Feb. 17–20, 1992, Washington, D.C.

BENZOTHIOPHENES FOR BONE HEALING AND FRACTURE REPAIR

BACKGROUND OF THE INVENTION

Approximately, 20–25 million women and an increasing number of men have detectable vertebral fractures, with an additional 250,000 hip fractures reported yearly in America alone. The latter case is associated with a 12% mortality rate within the first two years and with a 30% rate of patients requiring nursing home care after the fracture. While this is already significant, the economic and medical consequences of convalescence due to slow or imperfect healing of these bone fractures is expected to increase, due to the aging of the general population. While there are several promising therapies (bis-phosphonates, Tamoxifen, etc.) in development to prevent bone loss with age and thus reduce the probability of incurring debilitating fractures, these therapies are not indicated for treatment once the fracture has occurred.

Estrogens have been shown (Bolander et al., 38th Annual Meeting Orthopedic Research Society, 1992) to improve the quality of the healing of appendicular fractures. Therefore, estrogen replacement therapy would appear to be a method for the treatment of fracture repair, as is for post-menopausal osteoporosis. However, patient compliance with estrogen therapy is relatively poor due to its side effects, including the resumption of menses, mastodynia, an increased risk of uterine cancer, an increased perceived risk of breast cancer, and the concomitant use of progestins. In addition, men are likely to object to the use of estrogen treatment. Clearly the need exists for a therapy which would be beneficial to patients who have suffered debilitating bone fractures and which would increase patient compliance.

SUMMARY OF THE INVENTION

This invention provides methods of facilitating bone healing and fracture repair comprising administering to a human in need thereof an effective amount of a compound of formula I

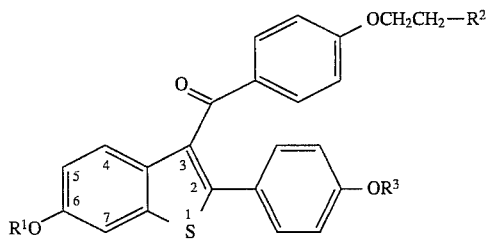

wherein $R^1$ and $R^3$ are independently hydrogen,

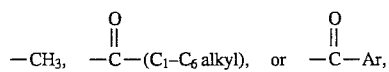

wherein Ar is optionally substituted phenyl; $R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for facilitating bone healing and fracture repair. Raloxifene and selected analogs are nuclear regulators which share certain physiological effects with estrogens, particularly in bone homeostasis, but are essentially devoid of the uterine and breast effects of estrogens. Additionally, raloxifene has a greatly reduced potential for feminization in men than estrogens.

The therapeutic and prophylactic, such as given prior to surgery requiring or causing bone damage, treatments provided by this invention are practiced by administering to a human in need thereof a dose of a compound of formula I or a pharmaceutically acceptable salt or solvate thereof, that is effective to facilitate bone healing or fracture repair.

Raloxifene is a preferred compound of this invention and it is the hydrochloride salt of a compound of formula 1 wherein $R^1$ and $R^3$ are hydrogen and $R^2$ is 1-piperidinyl.

Generally, at least one compound of formula I is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. The term "optionally substituted phenyl" includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to facilitate bone healing and fracture repair, according to this invention, will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed, and for a duration, to effectively treat the patient.

It is usually preferred to administer a compound of formula I in the form of an acid addition salt, as is customary in the administration of pharmaceuticals bearing a basic group, such as the piperidino ring. For such purposes the following oral dosage forms are available.

FORMULATIONS

In the formulations which follow, "Active ingredient" means a compound of formula I.

| Formulation 1: Gelatin Capsules<br>Hard gelatin capsules are prepared using the following: | |
|---|---|
| Ingredient | Quantity (mg/capsule) |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

| Ingredient | Quantity (mg/capsule) |
|---|---|
| Formulation 2: Raloxifene capsule | |
| Raloxifene | 1 |
| Starch, NF | 112 |
| Starch flowable powder | 225.3 |
| Silicone fluid 350 centistokes | 1.7 |
| Formulation 3: Raloxifene capsule | |
| Raloxifene | 5 |
| Starch, NF | 108 |
| Starch flowable powder | 225.3 |
| Silicone fluid 350 centistokes | 1.7 |
| Formulation 4: Raloxifene capsule | |
| Raloxifene | 10 |
| Starch, NF | 103 |
| Starch flowable powder | 225.3 |
| Silicone fluid 350 centistokes | 1.7 |
| Formulation 5: Raloxifene capsule | |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Formulation 6: Tablets | |
|---|---|
| Ingredient | Quantity (mg/tablet) |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of Active ingredient are made up as follows:

| Formulation 7: Tablets | |
|---|---|
| Ingredient | Quantity (mg/tablet) |
| Active ingredient | 0.1–1000 |
| Starch | 45 |
| Cellulose, microcrystalline | 35 |
| Polyvinylpyrrolidone<br>(as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

| Formulation 8: Suspensions | |
| --- | --- |
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

ASSAYS

Assay 1

Six month old, virgin Sprague-Dawley female rats (Harlan, Ind.) weighing about 270 g are maintained on a 12 hr light/dark cycle at 22° C. with ad lib access to food (TD 89222 with 0.5% Ca and 0.4% P, Teklad, Madison, Wis.) and water. Bilateral ovariectomies are performed for multiple sets of rats, except for SHAM controls, at 6 months of age. Rats are grouped into treatment units of n=9 per set and orally dosed daily for 28 days to include: 1) sham-operated control (SHAM), 2) ovariectomized control (OVX), 3) OVX treated with a compound of formula 1. The proximal tibiae are scanned longitudinally to confirm ovariectomy induced bone loss and efficacy of treatment. Multiple sets of rats are followed longitudinally to yield about 200 rats per group by the end of the study.

At 28 days post-ovariectomy, both femora are pinned and one of the femora is fractured, as described in Bonnarens et al., 1984, J. Orthopaedic Research 2:97–101. Transverse fractures are compared to pinned controls by x-ray analysis, and daily dosing of rats is continued for an additional 42 days. Fracture calluses are collected at days 1–14 post-fracture and harvested for RNA to probe for treatment effects on the expression of specific genes by Northern analysis. At 70 days post-ovariectomy, the remaining rats are sacrificed to collect serum for cholesterol analysis, uteri to confirm efficacy of ovariectomy, both femora, and contralateral tibia for bone mass analysis by QCT. Both fractured and contralateral femora are x-rayed and biomechanically tested by torsional analysis to examine treatment effects on fracture healing, relative to contralateral controls. End points evaluated include treatment effects on TGF-β and estrogen receptor gene expression, x-ray analysis of fractures, bone mass measurements logitudinally and cross-sectionally, and biomechanical analysis for fractures.

Assay 2

Five to fifty women/are selected for the clinical study. The women have experienced bone damage, such as a fracture that has been initially treated in the conventional manner, i.e., resetting the bone, immobilization, or surgical procedure. The study has a placebo control group, i.e., the women are divided into two groups, one of which receives a compound of formula 1 as the active agent and the other receives a placebo. Women in the test group receive between 50–200 mg of the drug per day. They continue this therapy for 1–6 months. Accurate records are kept as to the status of the fracture repair. The results are compared both between members of each group and also the results for each patient are compared reported by each patient before the study began.

Utility of the compounds of formula I is illustrated by the positive impact they have in at least one of the assays described above.

We claim:

1. A method of facilitating bone healing or fracture repair comprising administering to a human in need thereof an effective amount of a compound having the formula

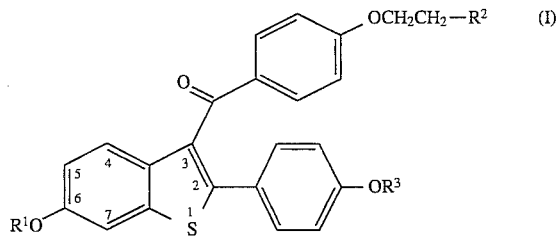

wherein $R^1$ and $R^3$ are independently hydrogen,

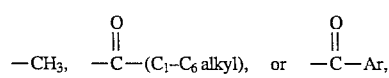

wherein Ar is optionally substituted phenyl;

$R^2$ is selected from the group consisting of pyrrolidine, hexamethylenemino, and piperidino; or a pharmaceutically acceptable salt of solvate thereof.

2. The method of claim 1 wherein said compound is the hydrochloride salt thereof.

3. The method of claim 1 wherein said compound is

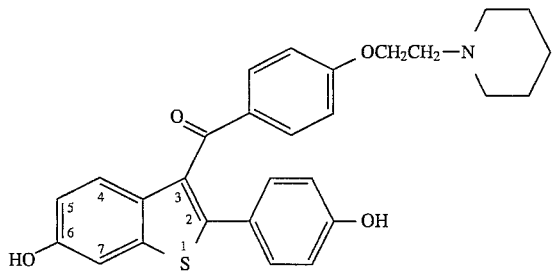

or its hydrochloride salt.

* * * * *